United States Patent [19]

Henco et al.

[11] Patent Number: 5,795,747
[45] Date of Patent: Aug. 18, 1998

[54] PROCESS FOR MANUFACTURING NEW BIOPOLYMERS

[75] Inventors: Karsten Henco, Erkrath; Manfred Eigen, Gottingen, both of Germany

[73] Assignee: Evotec Biosystems GmbH, Hamburg, Germany

[21] Appl. No.: 507,190

[22] Filed: Jun. 26, 1995

Related U.S. Application Data

[63] Continuation of Ser. No. 133,049, Dec. 7, 1993, abandoned.

[30] Foreign Application Priority Data

Apr. 16, 1991 [DE] Germany ............... 41 12 440.5

[51] Int. Cl.$^6$ ............................... C12P 19/34
[52] U.S. Cl. ........................ 435/91.1; 935/77; 935/78
[58] Field of Search ................... 435/6, 91.1, 91.2, 435/91.21; 935/77, 78

[56] References Cited

FOREIGN PATENT DOCUMENTS

| | | |
|---|---|---|
| 0285123 | 10/1988 | European Pat. Off. . |
| 9105058 | 4/1991 | WIPO . |
| 9202536 | 2/1992 | WIPO . |

OTHER PUBLICATIONS

C. Turek et al., "Systematic evolution of Liands by exponential enrichment: RNA ligands to bacteriophage T4 DNA polymerase", Science, vol. 249, Aug. 3, 1990, pp. 505–510.

M. Eigen, "Macromolecular Evolution: Dynamical Ordering in Sequence Space", Berichte Der Bunsen–Gesellschaft Für Physikalische Chemie, vol. 89, 1985, pp. 658–667.

D.L. Robertson et al., "Selection in vitro of an RNA enzyme that specifically cleaves single–stranded DNA", Nature, vol. 344, Mar. 29, 1990, pp. 467–468.

G.F. Joyce, "Amplification, mutation and selection of catalytic RNA", Gene, vol. 82, 1989, pp. 83–87.

*Primary Examiner*—Scott W. Houtteman
*Attorney, Agent, or Firm*—Jacobson, Price, Holman & Stern, PLLC

[57] ABSTRACT

The process of generating new biopolymers with improved characteristics, assisted by polymerases, is characterized in that at least one cycle of the steps described below, will be performed in a series of parallel preparations which are to be compared. Sequences of nucleic acids or, a mixture of similar sequences of nucleic acids in the distribution of mutants of a quasi-species, are subjected, in the region of the error threshold, to limited mutagenesis. These mixtures are replicated under simultaneous conditions and/or in succession. The mixtures of the so product nucleic acids are compartmentalized by segregation, and thereafter selected by a selection system which reflects the characteristics of interest of the nucleic acid sequence itself or, indirectly, via its translation product.

12 Claims, 4 Drawing Sheets

FIG. 1

| | Number of reaction compartments (rc) | Multiplicity of variants | Amplification/ Dilution | |
|---|---|---|---|---|
| Initial spectrum of variants | 1 | $10^9$ | | |
| Distribution | 1.000 | $10^6$ | | |
| Amplification($\times 10^6$) | 1.000 | $10^6$ | $10^6$ | 1. cycle |
| Selection | 1 | $10^6$ | $10^6$ | |
| Dilution ($\times 10^{-5}$) | 1 | $10^6$ | 10 | |
| Distribution | 1.000 | $10^4$ | | |
| Amplification($\times 10^6$) | 1.000 | $10^4$ | $10^6$ | 2. cycle |
| Selection | 1 | $10^4$ | $10^6$ | |
| Dilution ($\times 10^{-5}$) | 1 | $10^4$ | 10 | |
| Distribution | 1.000 | $10^2$ | | |
| Amplification($\times 10^6$) | 1.000 | $10^2$ | $10^6$ | 3. cycle |
| Selection | 1 | $10^2$ | $10^6$ | |
| Dilution ($\times 10^{-5}$) | 1 | $10^2$ | 10 | |
| Distribution | 1.000 | 1 | | |
| Amplification($\times 10^6$) | 1.000* | 1* | $10^6$ | 4. cycle |
| Selection of a clone | 1 | 1 | $10^6$ | |

*Poisson-distribution

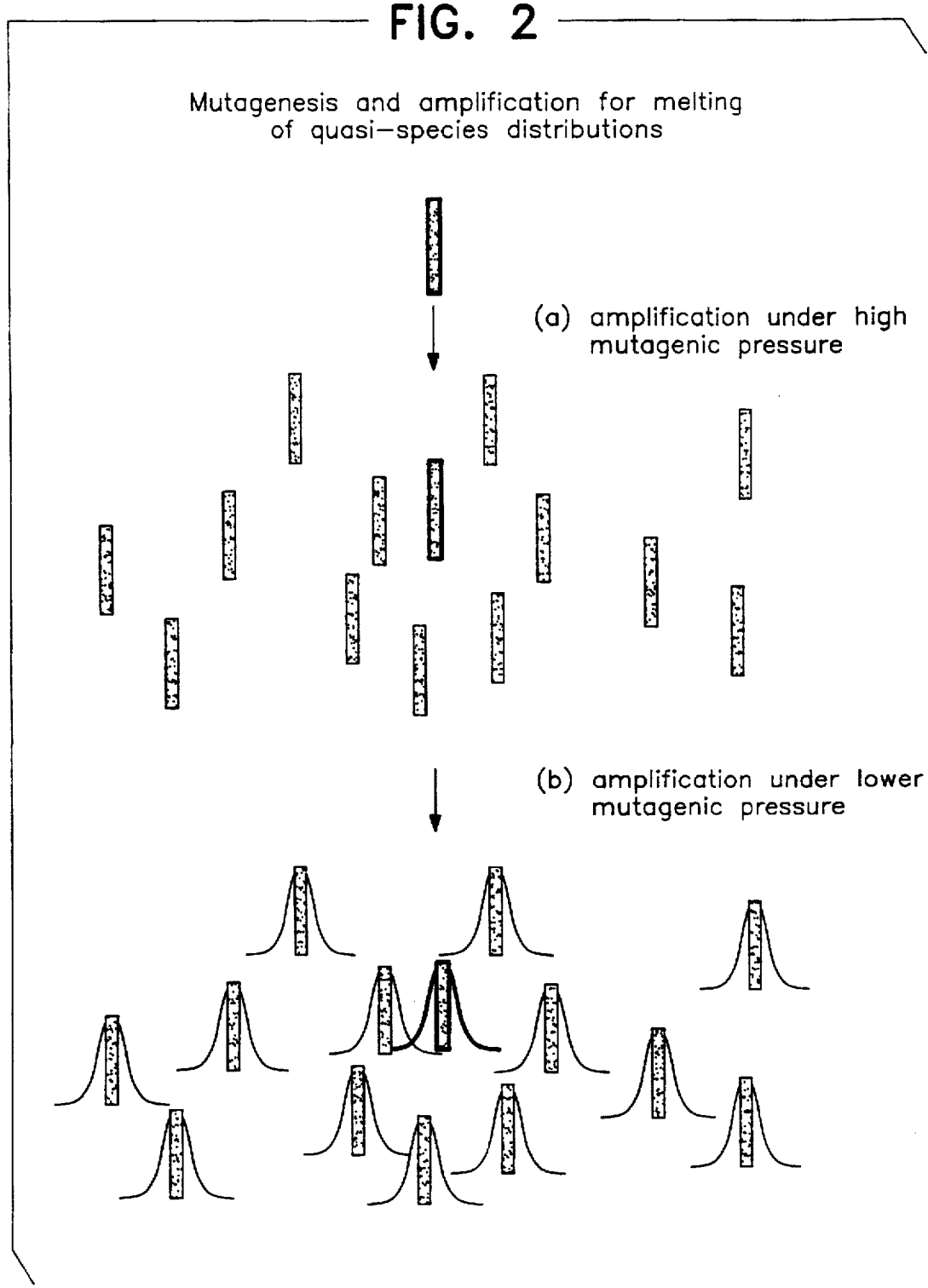

Cyclic product optimization

PROCESS FOR MANUFACTURING NEW BIOPOLYMERS

This application is a continuation of application Ser. No. 08/133,049, filed Dec. 7, 1993 now abandoned which is a 371 of PCT/EP92/00840 filed Apr. 14, 1992.

Biopolymers such as peptides, DNA and RNA are always synthesized with the help of polymerases. In the past, all sorts of biological resources have been screened extensively in order to obtain new biopolymers with improved functions, finally selecting out those with good or better functions in order to replicate them in large amounts for the purpose of manufacturing the desired biopolymers.

Ultimately, all classical methods for biological or microbiological culturing are based on this principle.

Considerable progress has been made already by the technique of genetic recombination and production of biopolymers in recombinant microorganisms and cell cultures. However, attempts of altering, specifically or nonspecifically, one or several parts of the biopolymers, or of their coding nucleic acid sequences respectively, were successful only in a few cases, in spite of the considerable effort and energy spent. L. Gold has described the optimization of a RNA molecule by one or two point mutations of equal value located within a small section of a sequence, using a process called SELEX. Nature demonstrates, however, that, frequently, more distant sections of sequences, or longer coherent sections of sequences, will become the subject of specific optimization. An example for this is the optimization of antibodies by mechanisms described as somatic mutations. Somatic mutations, although mechanistically not completely understood, show a significant increase in the selectivity of an antibody, thereby enlarging the genetic potential of coded antibodies beyond their capability of generating variants by recombination.

The optimization of biological pharmaceuticals is an eminent goal of the pharmaceutical industry. Worth mentioning are the optimization of enzymatic activities, of properties of receptors, of ligand interactions, of antibiotic or antiviral properties, of the efficacy of vaccination etc. Technologically, many possibilities are being pursued currently, such as screening methods for naturally existing structures or their chemical modifications, or goal-oriented design by computer-modelling, or procedures of recombinant genetic engineering.

Nature reveals to us the results of a natural optimization process, i.e., the results of evolution. To understand the mechanisms has been the goal of many famous scientists and philosophers. In the following, we will try to analyse briefly, in a few sentences, the ideas of Darwin ("The origin of Species", G. G. Simpson, Collier McMillan, London 1962), Monod ("Zufall und Notwendigkeit", J. Monod, Piper, München, 1971), and Eigen (M. Eigen, J. McCaskill & P. Schuster, 1987, 1988, J. Phys. Chem.). In his studies of the species, Darwin came to the result that evolution is based on the interplay between mutation and natural selection. Monod incorporated these considerations into the new concept of molecular genetics and discussed the importance of random mutations for the genetic information of an existing wild-type and the inevitability of subsequent selection if, and when, the mutant represents a better adapted function.

As a conclusion from simple reflections, M. Eigen could demonstrate that the natural process of optimization in evolution cannot be explained by mutagenesis of the wild-type. In other words, blind testing (trial-and-error) of naturally developing wild-type mutants would never lead to efficient evolution, in view of the astronomically high number of potential alternatives. The period of about 4 thousand millions years elapsed would be too short, and the available matter too small, by order of magnitudes, for creating whatever primitive forms of life. The breakthrough in understanding evolutionary processes occurred by the accurate interpretation of genetic experiments as well as by introduction of new concepts, such as quasi-species, sequence space, value landscape, hypercycle, compartmentalization.

The present invention, by necessity, requires explanation of some of these terms because they are inevitable for the translation, according to the claimed invention, into economically useable strategies for syntheses.

"Quasi-species" designates a new understanding of the old "wild-type" definition. The entirety of a collection of genomes which developed one from another by reduplication, is by no means a collective of identical "wild-type" sequences. It is rather a distribution of mutants surrounding the wild-type. Subject of selection is this very distribution, rather than the specific "wild-type" sequence. The distribution itself is, first of all, a result of copying errors caused by the enzymes involved in reduplication (polymerases). Only the most frequently represented mean sequence is identical with the formerly postulated "wild-type", whereas the great majority of all other sequences shows more or less significant deviations from the formerly defined wild-type sequence. The frequency of a specific sequence and the frequency of closely related sequences are a measure for their biological values. The distribution determines the so-called value-landscape. The evolutionary advantage is obvious: A biological system so structured can react very quickly to a changed profile of requirements. Even if, initially, they may not be well represented in number, variants do exist which differ rather widely from the wild-type but are closer to the hypothetical maximum of a new value. By this fact, evolution is provided with an internal guidance mechanism and, therefore, substantial time can be gained. Counter to this positive effect is the danger of a loss of information as a result of too high a frequency of errors occuring during replication. Eigen showed that natural systems replicate closely below a tolerable error maximum. An irreversible melting away of genetic information is prevented whereas, the flexibility of adaptation to changes is at maximum. The quasi-species will remain stable as long as no better adapted distribution emerges. A further consequence of this new understanding of value-landscapes is: Blind "trial-and-error" processes of mutagenesis are not necessary. Much rather are evolutionary adaptations moving goal-directed along the "ridges" of the fitness value landscape.

Hypercycle and compartmentalization are other terms which are to be translated by the invention onto a technological scale; their meaning must be shortly explained. The hypercycle is a cyclic interaction between carriers of information capable of replication and replication-catalysing enzymes coded by those carriers. Compartmentalization into vesicles or cell structures enables variants of hypercycles to evolve individually, and of mutations occurring statistically and regularly, which would prevent them from a direct and specific feed-back on their coding sequences.

The object of the invention is to develop, utilizing the above described insights, a process for generating new biopolymers with systematically improved properties, assisted by polymerases. This is to be resolved by performing at least one cycle of the following steps in a series of parallel preparations which are to be compared:

sequences of nucleic acids or a mixture of similar sequences of nucleic acids in a mutant distribution of a quasi-species, are submitted to limited mutagenesis in the region of the error threshold.

these mixtures are replicated under simultaneous conditions and/or in succession.

the mixtures of the so produced nucleic acids are separated by compartmentalization.

and, thereafter, selected by a selection system, either directly reflecting the characteristics of the nucleic acid sequence which are of interest, or indirectly, through its translation-product.

BRIEF DESCRIPTION OF THE DRAWINGS

FIG. 1 describes the combined hierarchical parallel processing and selection as well as the respective numerical examples of screening of a large selected spectrum of mutants.

FIG. 2 illustrates the strategy for mutagenesis and amplification in respect to the melting of quasi-species distributions.

Figure 3:
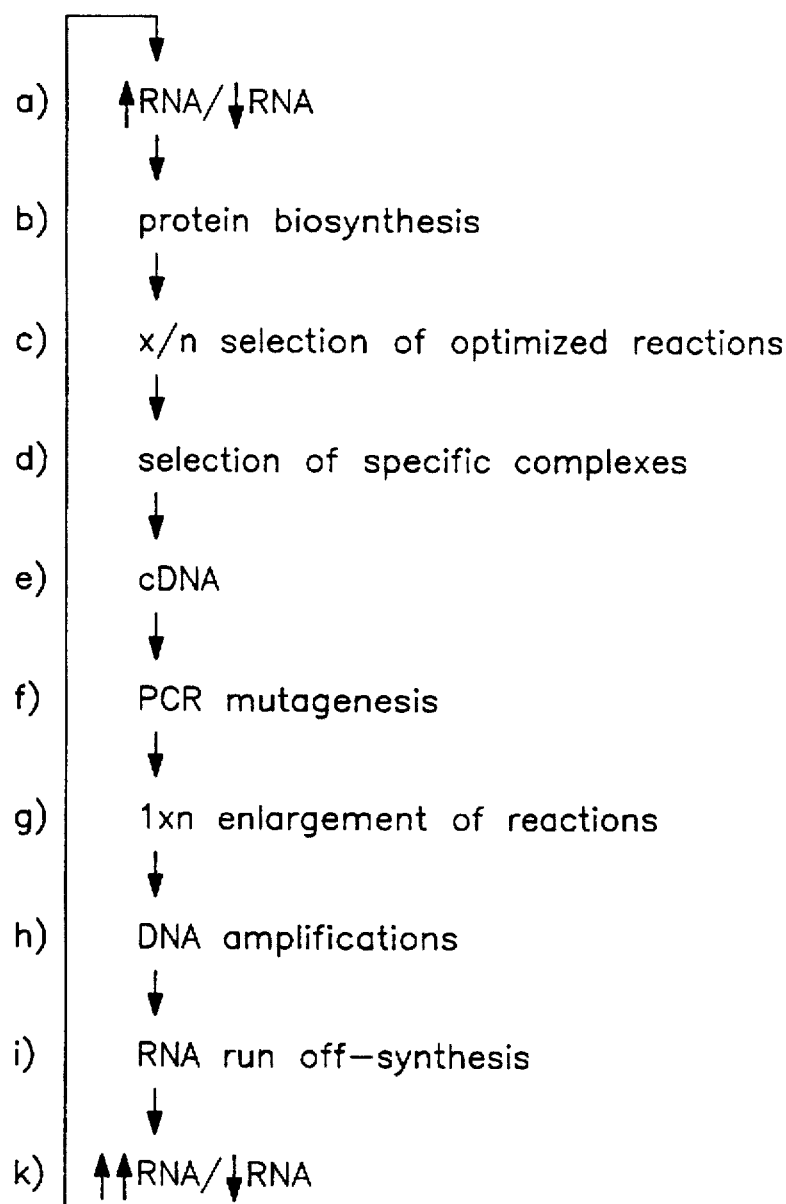
FIG. 3 shows a typical cyclic product optimization.

In the simplest case, mutagenesis occurs already by replication in the region of the error threshold of the replication enzyme/enzyme system. Also, it may be effected by reaction conditions and reaction parameters favourable for mutations, in order to reach, or even somewhat exceed, the region of the error threshold tolerable for a certain segment of a gene. To these belong, for instance, defined imbalanced dosages of purine- and/or pyrimidine nucleotide bases as well as the adding of base analogues. Furthermore, mutagenic substances and/or high-energetic radiation may be applied. Finally, other parameters such as temperature, pH-value, redox potential etc. may favour mutations.

Limited mutagenesis, in the sense of the present invention, is to be understood as a type of mutagenesis which does not lead to a complete destruction of the system. Further, it does not intent to effect an alteration of all parts of the nucleic sequence. This does not mean, though, that for arts of the mixture and for a short period of time, the biological limit set by the error threshold could not be exceeded. It is entirely acceptable that, besides survivable and possibly optimized mutants, also defect mutants may be produced which will not survive in the end. In any case, however, it is not intended that only a single mutant does survive —it must be groups of mutants which survive. Over and above, the conditions for mutagenesis may be so chosen or staged that different sequences of nucleic acids may be exposed to a varied mutagenic pressure. But also in this case, the survival of groups of mutants must be assured.

Preferably, mutagenesis is to take place in such a way that, by adjusting the accuracy of replication used as a variable or, by gradating the accuracy in consecutive steps in the region of the error threshold (tempering), followed by more exact (>>10) replicative amplification, the distribution of the nucleic acids will be guided, always in the region of its error threshold, through the value-landscape in the direction of the desired optimum.

The segregation into compartments must, according to the invention, be effected in such a way that, on the one hand, virtually all new and all old variants are present in at least one compartment and that on the other hand, the contents of the compartments can be differentiated by phenotypic selection. Such conditions can be determined, from "case to case" by rather simple pre-tests. Suitable compartments, for instance, are the compartments used in the replication machines according to Eigen; see German utility models 88 13 773.2 U1 ("Verschiebeeinheit"), 88 14 398.8 U1 ("Gradientenbrett"), DE 40 22 792.8 ("Folie"), DE 40 22 793.6 ("Verschweißeinrichtung") , DE 40 22 794.4 ("Form d. Folie") and DE 40 29 004.2 ("Schlitten").

With regard to the practical execution of the procedure, it is further important that those sequences of nucleic acids, which belong to a certain phenotypically selected group of biopolymers, can be assessed either simultaneously, or later on singularly, or in a mixture. This is of necessity in order to recover the optimized nucleic acid sequences established according to the invention, and to use them selectively for further cycles.

In contrast to classical methods of genetic engineering, neither the exact nucleic acid sequences of the initial population nor the exact nucleic acid sequences of the optimized population are determined, according to the invention. Instead, further progressing will be effected based on the degree of variation of selected groups by mutagenesis and selection. Thereby the ridge walking of nature in evolution is used, and so, the total process will be accelerated and simplified.

Selection from mixtures of nucleic acids is preferably performed on products in which genotypes and phenotypes are directly coupled. An example are polysomes containing, directly coupled, the translation products as well as the coding RNA.

Groups of such polysomes usually may be selected, for instance, according to their biological significance, by using, for example, their binding property to certain receptors, such as antibodies, metal chelates etc. The relevant nucleic acid sequence is, in its turn, still coupled to these polysomes. Therefore, it may be classed later on in a very simple way. Other usual selection methods, of course, can be employed as well. For example, such screening of a large mutant spectrum can be performed also on Eigen's apparatuses. Selection of one single clone from an initial spectrum of $10^9$ variants is so possible in no more than 4 cycles in this apparatus. The numerical ranges in which this selection can be performed sensibly and efficiently, are indicated in the attached FIG. 1, describing combined hierarchical parallel processing and selection as well as the respective numerical examples of screening of a large selected spectrum of mutants. Methods using fluorescence detection have found to be particularly well suited as detection procedures.

When a mutant distribution demonstrates relevant properties, hierarchical parallel processing allows a large spectrum of mutants to be screened. In the example of a multiplicity of $10^9$ variants, the stage of a pure culture is reached already after 4 selection cycles.

In order to avoid, with high statistical probability, any loss of variants, so many mutants are transferred, after amplification, to the next cycle, that each of the selected variants is represented about 10 times. For numerical values <<10, the stochastic effect would come into play so that losses of variants would occur easily. Conversely, an average representation of 100 copies of each variant would inhibit the selection effect, or would cause a reduction of the number of variants, respectively.

For performing the process according to the invention, the conditions have to be chosen so as to satisfy the following requirements:

Reaction chain, performed in cycles, with externally controllable monitoring of biological functions and selection;

reproducible handling of large numbers of samples;

avoidance, if possible, of recombinant organisms;

cyclic, artificially induced broadening of the mutant spectrum by means of region-selective mutagenesis;

on-line control of the optimization process;

potential for generation of statistical distributions of large quasi-species populations;

optimization of the population along ridges of the value-landscape;

hierarchical parallel processing of large numbers of sample preparations.

With this, the process according to the invention distinctly differentiates itself from the procedures known up to now. The idea of selecting well adapted substructures from a collective of mutants provided in a randomized form has already been proposed by Rechenberg 1973 ("Evolutionsstrategie", Problemata frommannholzboog, Stuttgart—Bad Cannstadt). C. Tuerk and L. Gold (1990), Science 249, 505 –510, were able to show also experimentally that this procedure is successful, if the number of possible mutants, i.e., if the number of positions to be varied, is small and, therefore, all potential variants are represented a priori in one mixture. This means, however, for a collective of say $10^{12}$ molecules, about 18 positions on the DNA/RNA level, vary provided every possible sequence is represented by 10 molecules on average. This strategy allows, therefore, optimization of only very short regions. However, according to the invention, the target for selection is proteins in which long parts of sequences shall be optimized, whereby they are present as a group of mutant distributions. With an "a priori" distribution, an inconceivably large number of molecules would have to be dealt with. This cannot be successful for different reasons, particularly for reasons of disproportionally large expenditures. Again, all dimensions of material and time available would be exceeded.

Also, the so-called "serial transfer" procedures are at least not practicable in the form so far published in literature, given that, for the step of selection and evaluation of a specific mutant, a dilution down to the level of a single copy is a prerequisite. Technically, no sufficient number of mutants can be tested and evaluated with these procedures. According to the invention, however, nature's principle is utilized in which better adapted mutants neither correspond to a homogeneous sequence spectrum nor to a defined wild-type sequence. Nature rather operates with mutant distributions and with weighting a quasi-species. Up to now this principle has never been applied to goal-directed development, and determination of selection values. For the same reason, no attention has been paid to the value-landscape surrounding the quasi-species, including those mutants with large Hamming-distances. However, the invention suggests increasing the occupation density of the very population of mutants in greater distance to the most frequently occupied sequence and immediate environment. For this purpose, the occupation of the value-landscape by the quasi-species distribution is broadened i.e., "melted". "Melting" means a limited intentional overstepping of the tolerable limits for replication errors. The tolerable limit of errors (i.e., the rate of incorporation of non-"Watson-Crickpairs") is defined by the length of the sequence, and by the selection value of a quasi-species distribution, i.e. the vertical distribution of value profiles. Since the polymerases used have rates of misincorporation, which are typically low in relation to the sequences replicated in vitro, the mutagenic pressure must be artificially increased according to the invention.

Next, the stringency of the selection system has to be adjusted to the chosen mutation pressure. The stringency must be so great as to allow the occupation profile to follow the value-landscape and be maintained permanently—in contrast to the random equal distribution in the SELEX-procedure. The conditions, therefore, have to be also chosen in such a way as to enable also those mutants having large relative Hamming-distances to survive selection.

The concept of quasi-species, according to the invention, takes into account also to the density of occupation by so-called neutral mutants. Neutral, in the strictest sense, are only those mutants which are surrounded in their neighbourhood by equally valued mutants, meaning they exist altogether on a plateau in the value-landscape. This is true, however, only as an approximation. The value of a specific sequence is co-determined by the value and, thus, by the occupation of the neighbouring variants from which the very sequence of this mutant can be generated by replication and weak mutagenesis. Therefore, according to the invention, the conditions for mutagenesis and amplification should be so chosen as to maintain a sufficient occupation density of the value-landscape. The invention, therefore, differentiates between a mutagenesis step, which is to lead to the creation of variants with large Hamming-distances, and the replication step required for occupying the smaller Hamming-distances in the neighbourhood of far distant variants. This principle is demonstrated in the attached FIG. 2, illustrating the strategy for mutagenesis and amplification in respect to the melting of quasi-species distributions.

This schematic illustration describes the fate of a sequence from a mutant distribution after having overcome the preceding steps of selection and distribution. In the mutagenesis step, this sequence is melted in a "mutagenesis pulse", which means that mutants are created having a higher mean Hamming-distance from the initial mutants, compared to the one which would have resulted from the natural misincorporation rate of the polymerases involved. In order to be able to carry out a functional selection, the mutagenesis step is followed, according to the invention, by an augmentation amplification step. Here, mutagenic pressure significantly lower than in the mutagenesis step, is chosen in the experiment —in the extreme case so that it corresponds to the natural misincorporation rate of the polymerases used. As a result, a spectrum of mutants with low Hamming-distances appears surrounding each mean sequence of greatly divergent variants.

Processes useful for the described course of action are automated gene-amplification procedures, which can be operated in cycles, or in alternating cycles, and which allow processing of large collectives of samples. For this purpose, PCR-capable systems and/or serial transfer-systems have been developed allowing transfer and selection of very large quasi-species distributions. The capability for handling unusually large collectives of samples, and the possiblity of their evaluation by means of suitable selection systems, are prerequisites for the translation of the invention into a technology practicable in reality. Under certain conditions, other amplification procedures (e.g., J. Compton 1991, Nature 350, 91–92) can also be applied for the steps of amplification and mutagenesis.

With the film technology described for a strategy of gene-amplification, between $10^3$ and $10^6$ preparations can be evaluated in parallel. This means, ultimately, analysis and selection from up to $10^{13}$ and $10^{16}$ mutants per reaction cycle.

According to the invention, the interplay of selection pressure and mutagenic pressure will take care of a balance between, on the one hand, the melting of the contents of information into a continuum of the possibilities of occupation no longer manageable numerically, and the freezing of the system, on the other hand. This interplay is fine-tuned so as to allow an optimal drifting of the quasi-species toward the desired optimum. Although analysis of the process used by nature yields numerically valuable, order-of-magnitude indications for the choice of the experimental parameters fine-tuning has to be done in each case, according to the invention, because it correlates specifically with the respective profile of requirements and, may even change along the way of the optimization profile. In other words, both parameters have to be reconciliated over and over. They are reflecting the structures of the value-landscape prevailing at any time, that is, its canyons or the width of its ridges and mountain crests. Slight deviations of one parameter may be controlled by subsequent adjustment of the second parameter, thereby controlling the danger of an irreversible melting-away of the information caused, for example, by too high a mutagenic pressure in a late stage of the optimization process. This means factually, if the mutagenic pressure had been chosen too low, the selection pressure can be raised, and if the mutagenic pressure was chosen too high, the selection pressure may be reduced.

Of great significance for the adjustment of the parameters discussed is the choice of a selection procedure, which shall enable a controlled selection of quasi-species distributions. These parameters are to allow a correct measuring of the value of a population, that is, they shall be closely correlated with the desired optimum. Their signal/noise ratio must be sufficiently high to permit clear decisions in the parallel processing of experiments in an automated multi-channel-system. Fluorescence measuring methods are optimally suited for this purpose.

Preferably, selection pressures not directly related to the targeted optimum shall be excluded. Thus, if the speed of replication is to be excluded as a criterion, amplification enzymes and primers must be offered in abundance. In protein biosynthesis carried out in vitro, certain effects caused by the use of rare codons may be excluded.

According to the invention, the cycle is carried out at least once, preferably however, several times. FIG. 3 shows a typical cyclic product optimization. It may consist, for example, of the steps a) to k). Herein, information carrying RNA which is to be optimized is replicated and mutagenized by means of replicase, or by a PCR reaction, or by a homogenous RNA/DNA-replication process. In this process, for translation into the corresponding protein product, a promotor-sequence will be introduced, which may be inserted synthetically, for example, by means of a primer or a ligation procedure, thereby avoiding being subjected to the mutation step. For coupling genotype and phenotype, binding properties may be combined with a specific extraction, thereby increasing the efficiency of the selection step in a given cycle. Necessary, and also sufficient according to the invention, is the strategy of compartmentalization for hierarchical parallel processing of mutant distributions.

Figure 4:
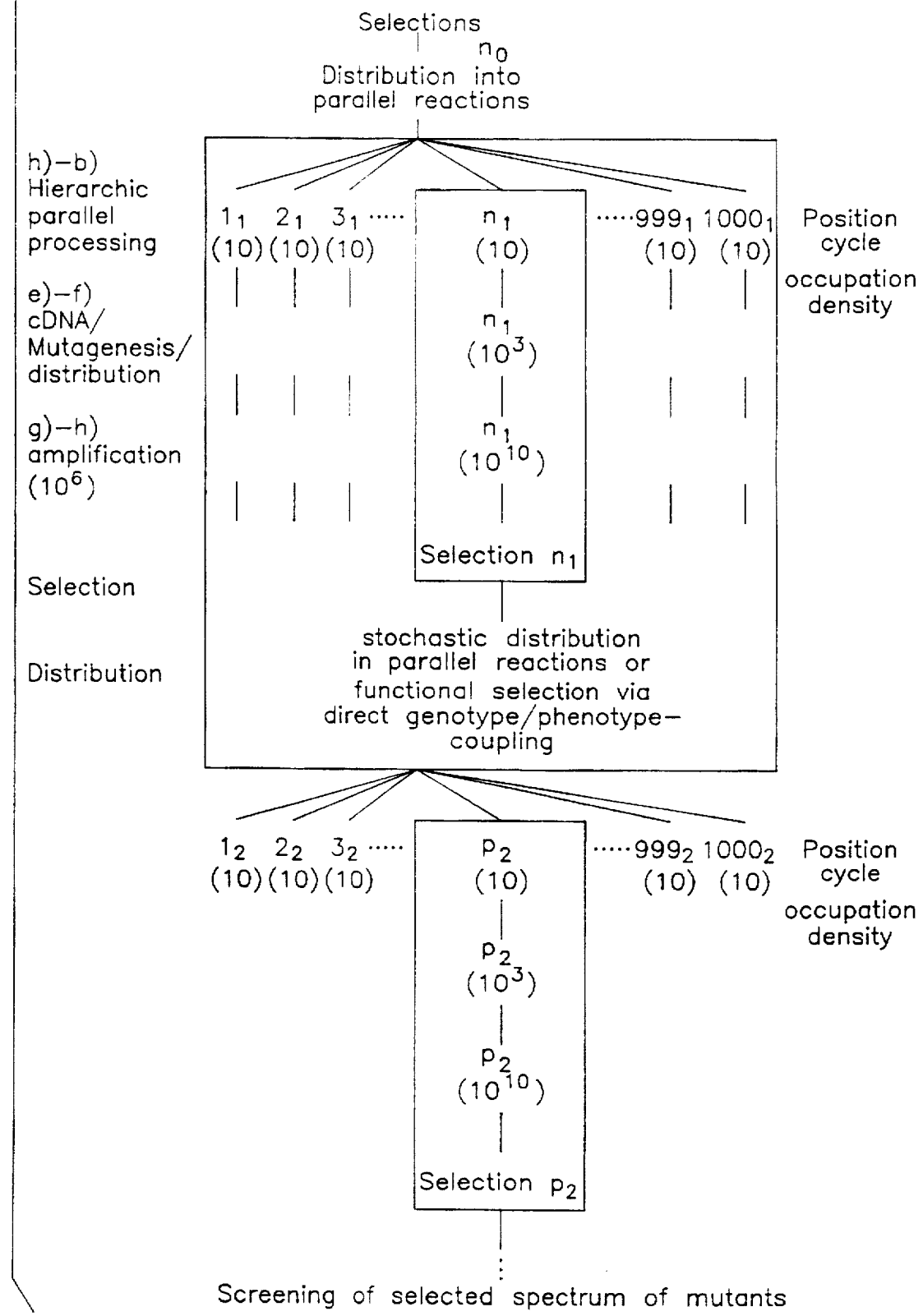
FIG. 4 shows a typical hierarchic parallel processing after selection.

FIG. 4 shows a typical hierarchic parallel processing after selection. The diagram illustrates a section of the chain of cyclic reaction sequences, and so explaines the hierarchic parallel processing according to the invention and, how it is related to the steps of mutation, amplification and selection. The numbers shown correspond to the process that is the subject of the invention. Nevertheless, they may differ considerably in reality. Their ranges, in orders of magnitude, must be so chosen in each case that optimized variants statistically have a high probability of being positively selected or, of reaching the next cycle respectively, optimized variants are discernible in the selection step from the background noise of inferior variants, the level of amplification allows a sufficiently high signal for measuring the selection parameter, and as many as possible different variants can be screened per each cycle.

An aliquot (mo) from a selected distribution of variants out of the cycle o, containing about 1,000 variants, is (re-)distributed in such a way into a certain number (for example 1,000) of reaction compartments (rc), that each rc will contain about 10 variants, in order for each variant to be represented about 10-fold in total. Thus, the probability of loosing a variant is statistically small. The re-distributions from the first cycle, $(1_1, 2_1, \ldots 1,000_1)$, are submitted in parallel to mutagenesis, whereby about $10^3$ variants will be created per rc. They are then amplified in such a way as to produce about $10^{10}$ sequences per rc consisting of the $10^3$ different variants after mutagenesis.

In the selection step, according to the invention, a reaction preparation $n_1$ is selected for the next cycle, however, not by valuation of $n_1$, but by valuation of the amplified mutant spectrum $n_1'$ derived from $n_1$. For the example of $10^3$ variants per rc, it is again sufficient if an aliquot is distributed in this way to 1,000 rc's of the next cycle $(1_2, 2_2 \ldots 1,000_2)$ so that on average, again each of the single variants from $n_1'$ is represented 10-fold in cycle 2. On the basis of the numbers proposed, $10^5$ variants per cycle would have to be screened. This number could be increased significantly, if either more rc's would be used, or a more sensitive or more stringent selection procedure would be applied, or if the desired defective mutants can be separated out from $n_1'$, for example by extraction, as it is possible, for example, in a selection process via optimizing of binding.

I claim:

1. A process of preparing new biopolymers with improved characteristics starting with nucleic acids comprising the steps of:

a) subjecting to limited mutagenesis in the range of the error threshold at least one sample of identical nucleic acid sequences or similar sequences of nucleic acids in the mutant distribution of a quasi-species to effect a mixture of nucleic acid sequences;

b) replicating, under less stringent mutagenic pressure than step (a), said mixture of nucleic acid sequences in said at least one sample to effect mutant distributions;

c) separating said mutant distributions into secondary samples;

d) repeating steps a)–c) in at least one cycle;

e) performing steps a) and b);

f) selecting at least one of said secondary samples based on phenotypic characteristics of the mutuant distributions in the secondary sample; and g) isolating from said selected secondary sample a mutagenized nucleic acid sequence based on its characteristics or the characteristics of its translation product.

2. The process according to claim 1, wherein steps a)–f) are repeated in at least one cycle before performing step g).

3. The process according to claim 1, wherein said limited mutagenesis is performed by (i) contacting the sample with a mutagenic agent or (ii) irradiating the sample.

4. The process according to claim 3, wherein the sample is contacted with an unbalanced dose of a mutagenic agent and wherein said mutagenic agent is selected from the group consisting of a purine and a pyrimidine nucleotide base, a base analog thereof, and a combination of the nucleotide base and nucleotide base analog.

5. The process according to claim 1, wherein the distribution of the nucleic acid sequences is guided in the range of the error threshold through the value landscape in the direction of a desired optimum (i) by adjusting the accuracy of replication used as a variable or by gradating the accuracy in consecutive steps in the range of the error threshold followed by (ii) >>10 times more exact replicative amplification.

6. The process according to claim 1, wherein the limited mutagenesis involves exposing different sections of the nucleic acids to different mutagenic pressures.

7. The process according to claim 1, wherein nucleic acid sequences in a secondary sample selected by phenotype are classified simultaneously or later on and further alone or in a mixture.

8. The process according to claim 1, wherein the mutagenized nucleic acid is isolated based on its translation product in which said mutagenized nucleic acid and said translation product are directly coupled.

9. The process according to claim 1, wherein said isolation is carried out using polysomes that bind, in a coupled form, said translation product and its coding mutagenized nucleic acid.

10. The process according to claim 1, wherein the selecting step is controlled, cycle by cycle, by varying the stringency of limited mutagenesis conditions and selecting conditions.

11. The process according to claim 1, conducted simultaneously on two or more samples.

12. The process according to claim 11, involving at least $10^3$ samples.

* * * * *

UNITED STATES PATENT AND TRADEMARK OFFICE
CERTIFICATE OF CORRECTION

PATENT NO. : 5,795,747
DATED : August 18, 1998
INVENTOR(S) : Karsten Henco et al.

It is certified that error appears in the above-identified patent and that said Letters Patent is hereby corrected as shown below:

Column 2,
Line 57, change "of" to -- avoids --;

Column 3,
Line 42, change "arts" to -- parts --;

Column 5,
Line 26, change "level, vary" to -- level vary, --;

Column 6,
Line 10, delete "to".

Signed and Sealed this

Eighteenth Day of September, 2001

Attest:

NICHOLAS P. GODICI
*Attesting Officer*    *Acting Director of the United States Patent and Trademark Office*